(12) United States Patent
Hsieh et al.

(10) Patent No.: US 8,673,658 B2
(45) Date of Patent: Mar. 18, 2014

(54) FABRICATING METHOD OF SEMICONDUCTOR DEVICE

(71) Applicant: Industrial Technology Research Institute, Hsinchu (TW)

(72) Inventors: Ming-Che Hsieh, Kaohsiung (TW); John H. Lau, Taipei (TW); Ra-Min Tain, New Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/769,824

(22) Filed: Feb. 19, 2013

(65) Prior Publication Data

US 2013/0171747 A1    Jul. 4, 2013

Related U.S. Application Data

(62) Division of application No. 13/023,545, filed on Feb. 9, 2011, now Pat. No. 8,397,584.

(30) Foreign Application Priority Data

Nov. 26, 2010  (TW) .............................. 99141042 A

(51) Int. Cl.
*H01L 21/12*    (2006.01)
(52) U.S. Cl.
USPC .......................................................... 438/14
(58) Field of Classification Search
None
See application file for complete search history.

(56) References Cited

U.S. PATENT DOCUMENTS

| 5,202,754 | A | 4/1993 | Bertin et al. |
| 8,397,584 | B2 * | 3/2013 | Hsieh et al. ..................... 73/849 |
| 2003/0012925 | A1 | 1/2003 | Gorrell |
| 2009/0191708 | A1 | 7/2009 | Kropewnicki et al. |
| 2010/0013512 | A1 | 1/2010 | Hargan et al. |
| 2010/0078655 | A1 | 4/2010 | Yang |
| 2010/0200989 | A1 | 8/2010 | Sprey et al. |

FOREIGN PATENT DOCUMENTS

| CN | 101853804 | 10/2010 |
| TW | 200620515 | 6/2006 |
| TW | 200631126 | 9/2006 |
| TW | 201015687 | 4/2010 |

OTHER PUBLICATIONS

"Notic of Allowance of Taiwan Counterpart Application", issued on Jun. 24, 2013, p. 1-p. 3.

* cited by examiner

*Primary Examiner* — Seahvosh Nikmanesh
(74) *Attorney, Agent, or Firm* — Jianq Chyun IP Office

(57) ABSTRACT

A fabricating method and a testing method of a semiconductor device and a mechanical integrity testing apparatus are provided. An object includes a wafer, an insulating layer, and a plurality of conductive posts is provided. A surface of the wafer has a plurality of first blind holes outside chip regions and a plurality of second blind holes inside the chip regions. The insulating layer is between the conductive posts and the walls of the first blind holes and between the conductive posts and the walls of the second blind holes. A mechanical integrity test is performed to test a binding strength between the insulating layer, the conductive posts, and the walls of the first blind holes. The conductive posts in the chip regions are electrically connected to an element after the conductive posts in the first blind holes are qualified in the mechanical integrity test.

11 Claims, 24 Drawing Sheets

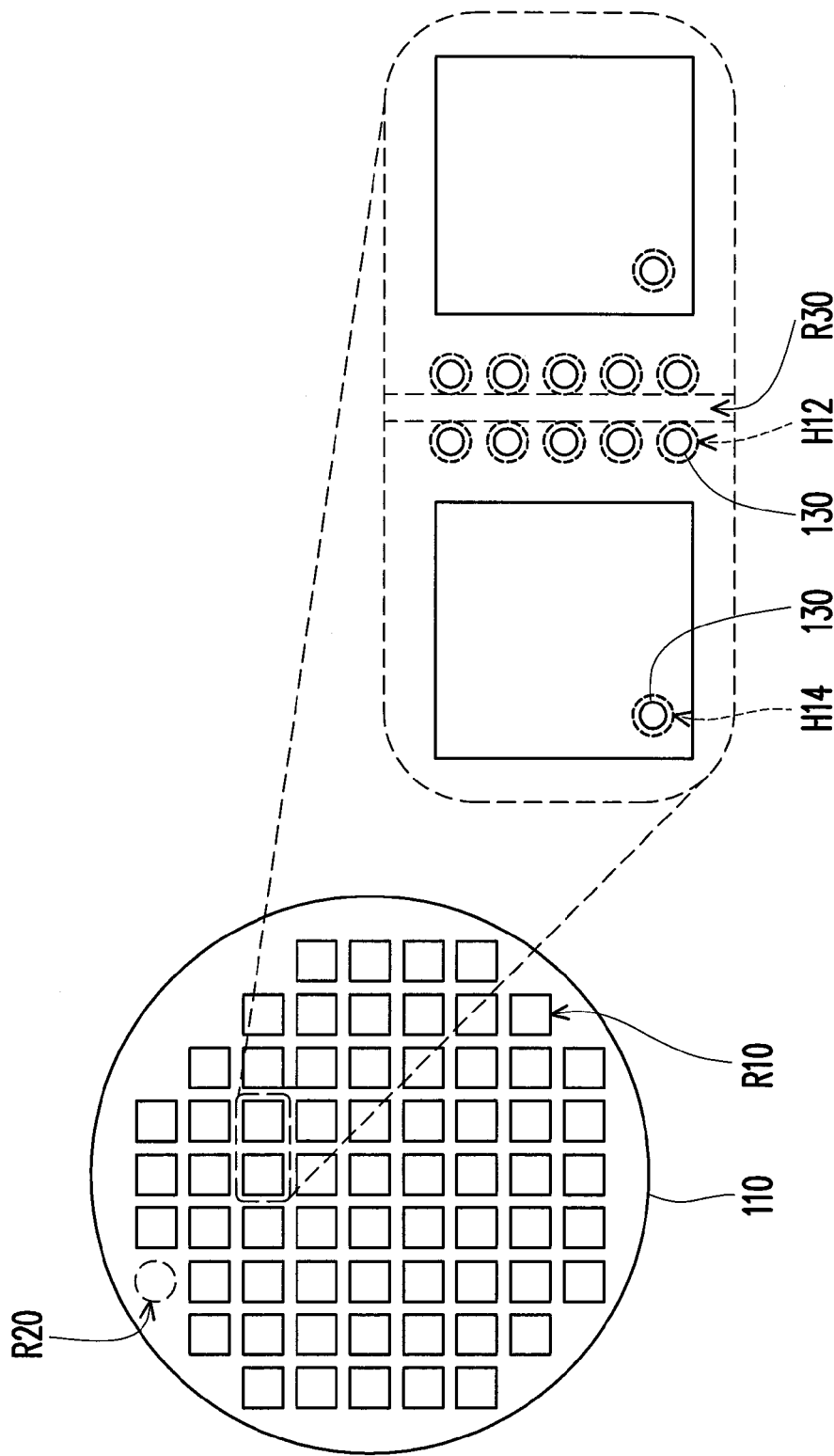

US 8,673,658 B2

FABRICATING METHOD OF SEMICONDUCTOR DEVICE

CROSS-REFERENCE TO RELATED APPLICATION

This application is a divisional application of and claims the priority benefit of U.S. application Ser. No. 13/023,545, filed on Feb. 9, 2011, now allowed as U.S. Pat. No. 8,397,584, which claims the priority benefit of Taiwan application serial no. 99141042, filed on Nov. 26, 2010. The entirety of each of the above-mentioned patent applications is hereby incorporated by reference herein and made a part of this specification.

TECHNICAL FIELD

The disclosure relates to a fabricating method, and to a fabricating method of a semiconductor device.

BACKGROUND

As functions of the computer and other communication products are quickly developed and improved, recently in industries related to the semiconductor, in order to meet the demands of diversification and micro-miniaturization of the electronic products and other functions, the chip packaging process increasingly departs from the conventional technique and is developed towards the high precision process having the high power, the high density, and the low cost, and being light, thin, short, and small, and a three-dimensional (3D) stacked integrated chip (IC) technique is developed to meet the demands. Although the concept of the 3D stacked IC has been proposed in several years ago, after the semiconductor process enters the nano-level, the most urgent problem to be solved is the yield of a through silicon via (TSV). It is the foremost topic in a reliability test how to test the integrity and the yield of the TSV. In the recent testing method, in most cases, the reliability test is performed after the 3DIC is already stacked, but usually the TSV structure is defective before the chip is stacked. If the defective TSV is used to perform the process of stacking the chip, the cost and the time are wasted and the process does not have the benefit. Therefore, it becomes quite important how to detect the integrity and the yield of the TSV before the chip is stacked.

In a conventional package testing method, usually a shear test is used to push a solder ball, so as to test the integrity of the solder ball of a ball grid array (BGA) structure, thereby obtaining the reliability of the solder ball according to whether a normative force of the solder ball is damaged. In addition, in the packaging structure using the wire bonding, the reliability is determined according to whether the wires are hooked by the hook to break. In a usual 3DIC integration process, as shown in FIG. 17, after electroplated copper TSVs are fabricated and Cu Chemical Mechanical Polishing/Planarization (CMP) is performed, the integrity of the TSV needs to be tested, but recently a TSV structure integrity testing apparatus and a testing method do not exist.

SUMMARY

A fabricating method of a semiconductor device is introduced herein, which includes the following steps: providing a wafer including a first surface and a second surface; forming a plurality of blind holes on the first surface of the wafer; forming an insulating layer on a wall of the blind hole and the first surface of the wafer; forming a conductive post in the blind hole, and enabling a first surface of the conductive post to be exposed out of the insulating layer; and providing an external force to the first surface of the conductive post, and determining a mechanical integrity of the conductive post according to whether the conductive post is damaged.

Several embodiments accompanied with figures are described in detail below to further describe the invention in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

FIG. 3 is a top view of an object to be tested of FIG. 2D.

DETAILED DESCRIPTION OF DISCLOSED EMBODIMENTS

Figure 1:
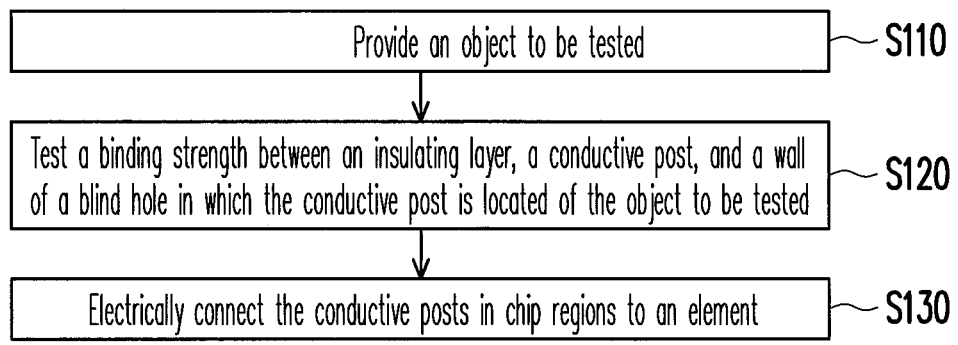
FIG. 1 is a flow chart of a fabricating method of a semiconductor device according to an embodiment of the disclosure.

FIG. 1 is a flow chart of a fabricating method of a semiconductor device according to an embodiment of the disclosure. Referring to FIG. 1, the fabricating method of the semiconductor device according to this embodiment includes the following steps: providing a wafer including a first surface and a second surface; forming a plurality of blind holes on the first surface of the wafer; forming an insulating layer on a wall of the blind hole and the first surface of the wafer; forming a conductive post in the blind hole, and enabling a first surface of the conductive post to be exposed out of the insulating layer; and providing an external force to the first surface of the conductive post, and determining a mechanical integrity of the conductive post according to whether the conductive post is damaged. It may be known from the above content that in the fabricating method of the semiconductor device according to this embodiment, it is firstly confirmed that the conductive post has the qualified integrity, and then, the conductive posts in chip regions on the same object to be tested are used to perform subsequent processes. In this manner, probabilities that a fabricated semiconductor device is defective due to the defective conductive posts are reduced, so as to lower a fabricating time and a fabricating cost. In the following, more embodiments are listed, but the disclosure is not limited hereto. In the disclosure, a random sampling test may be performed, or a test may be arranged during the process. In the random sampling test, a yield of the conductive post of the wafer is tested in batches, so as to determine whether the batch of wafers is available. If the test is performed during the process, each wafer may be more directly selected with more helps. No matter which manner is used, it falls within the protection scope of the disclosure.

Figure 2A:
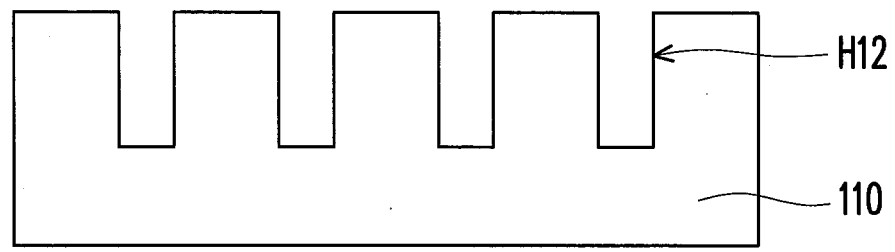
FIGS. 2A to 2O are schematic partial cross-sectional views of a fabricating method of a semiconductor device according to another embodiment of the disclosure.
Figure 2B:
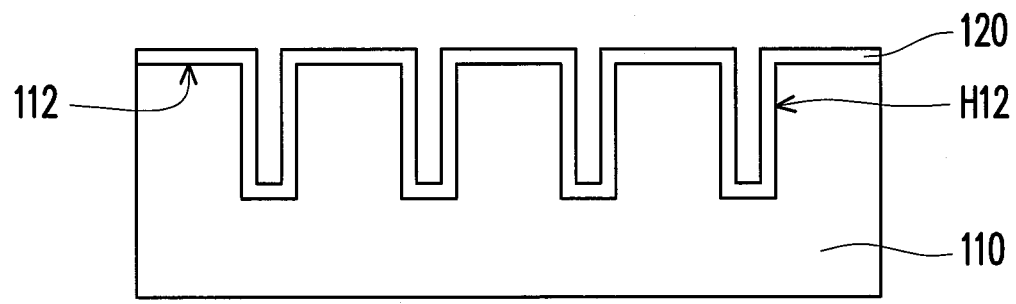
Figure 2C:
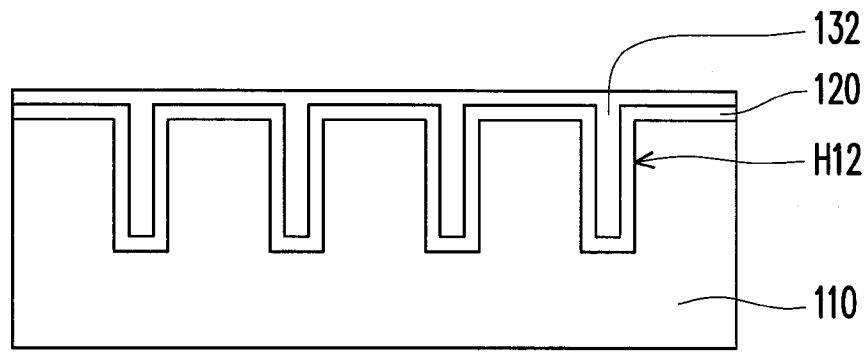
Figure 2D:
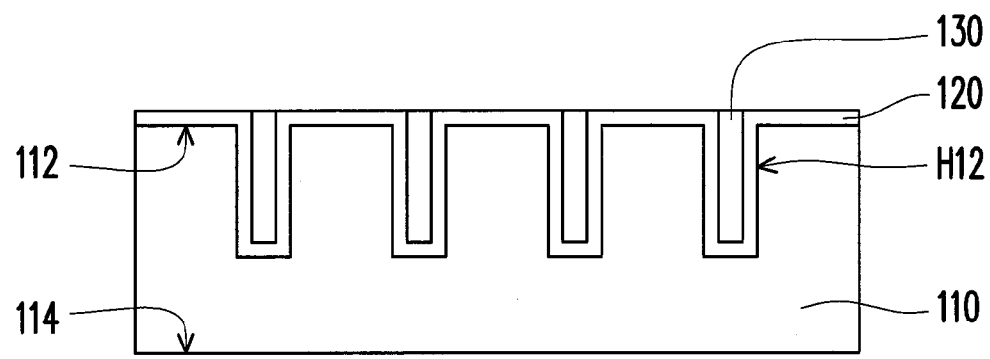

FIGS. 2A to 2O are schematic partial cross-sectional views of a fabricating method of a semiconductor device according to another embodiment of the disclosure, and FIG. 3 is a top view of an object to be tested of FIG. 2D. Referring to FIGS. 2A to 2C, before the object to be tested 100 of FIG. 2D is prepared, firstly a complete wafer 110 is cleaned, and a plurality of blind holes, for example, first blind holes H12 and second blind holes H14 of FIG. 3, is formed on a first surface of the wafer 110 through a lithographically etching process. Then, an insulating layer 120 is formed on the first surface of the wafer 110 and a wall of the blind hole, as shown in FIG. 2B. Next, a conductive layer 132 is formed on the insulating layer 120 of the wafer 110, and the conductive layer 132 fills inside the first blind holes H12 and the second blind holes H14 of FIG. 3, as shown in FIG. 2C. A material of the conductive layer 132 is, for example, copper or other conductive materials. Afterwards, a part of the conductive layer 132 is removed through a CMP process or other processes, so as to form conductive posts 130 filling inside the first blind holes H12 and the second blind holes H14 of FIG. 3, and a first surface of the conductive post 130 is enabled to be exposed out of the insulating layer 120, as shown in FIG. 2D. In FIGS. 2A to 2D, a process of forming the first blind holes H12, the insulating layer 120 and the conductive posts 130 of the corresponding region are described. However, before, after or during the steps, various lines and elements required by the chips may be formed in chip regions R10 of the wafer 110 as shown in FIG. 3, and the conventional art is not described here.

Referring to FIGS. 2D and 3, in the fabricating method of the semiconductor device according to this embodiment, firstly, an object to be tested 100 is provided, and FIG. 2D shows a partial cross section of the object to be tested 100. The object to be tested 100 includes a wafer 110, an insulating layer 120, and a plurality of conductive posts 130. The wafer 110 has a first surface 112 and a second surface 114 opposite to each other, as shown in FIG. 2D-2J. The wafer 110 includes a plurality of chip regions R10, as shown in FIG. 3. The first surface 112 has a plurality of first blind holes H12 and a plurality of second blind holes H14. The first blind holes H12 are outside or between the chip regions R10, the second blind holes H14 are inside the chip regions R10. The insulating layer 120 covers the first surface 112, walls of the first blind holes H12, and walls of the second blind holes H14, but FIG. 2D does not show that the insulating layer 120 covers the walls of the second blind holes H14. The conductive posts 130 fill inside the first blind holes H12 and the second blind holes H14, the insulating layer 120 is between the conductive post 130 and the wall of the first blind hole H12, and the insulating layer 120 is also between the conductive post 130 and the wall of the second blind hole H14.

FIG. 3 shows positions of the first blind holes H12 between two chip regions R10 through magnification, but the first blind holes H12 may also be on peripheral regions of the wafer 110 or other regions except for the chip regions R10, for example, a region R20. The position of the first blind hole H12 may be designed to be away from a cutting channel R30. The cutting channel R30 is a region through which a cutter passes when cutting the object to be tested 100 into a plurality of chips. The conductive posts 130 in the first blind holes H12 on both sides of the cutting channel R30 are purely used to test a yield, and may be removed or kept after the test. Alternatively, the first blind holes H12 may also be directly designed to be in the cutting channel R30, and the conductive posts 130 in the first blind holes H12 may be used to test the yield before the cutting, and may be removed during the cutting.

Figure 2E:
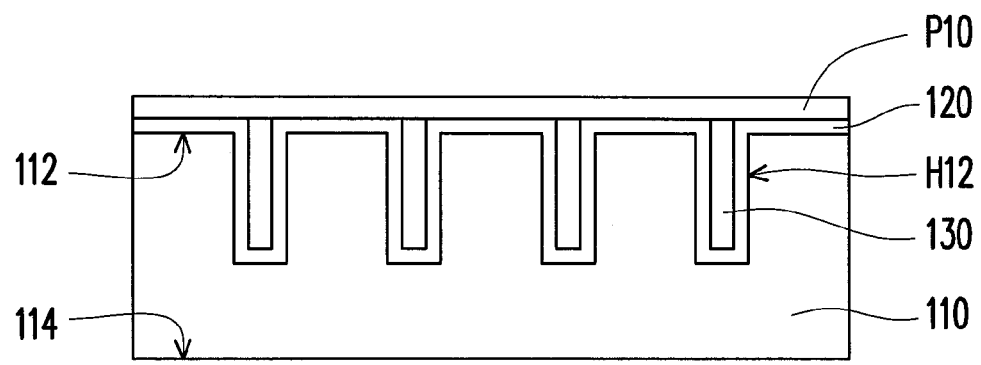
Figure 2F:
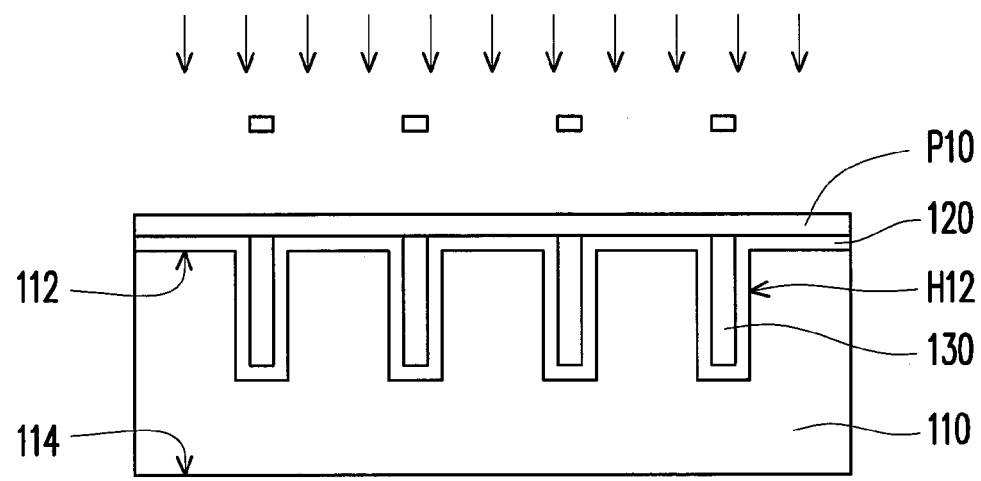
Figure 2G:
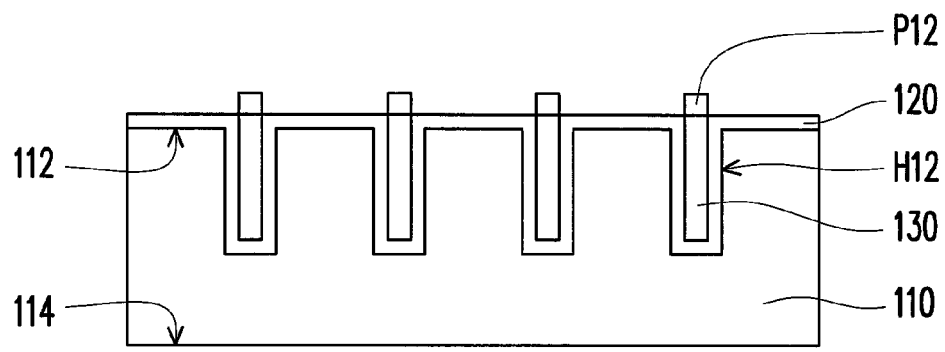
Figure 2H:
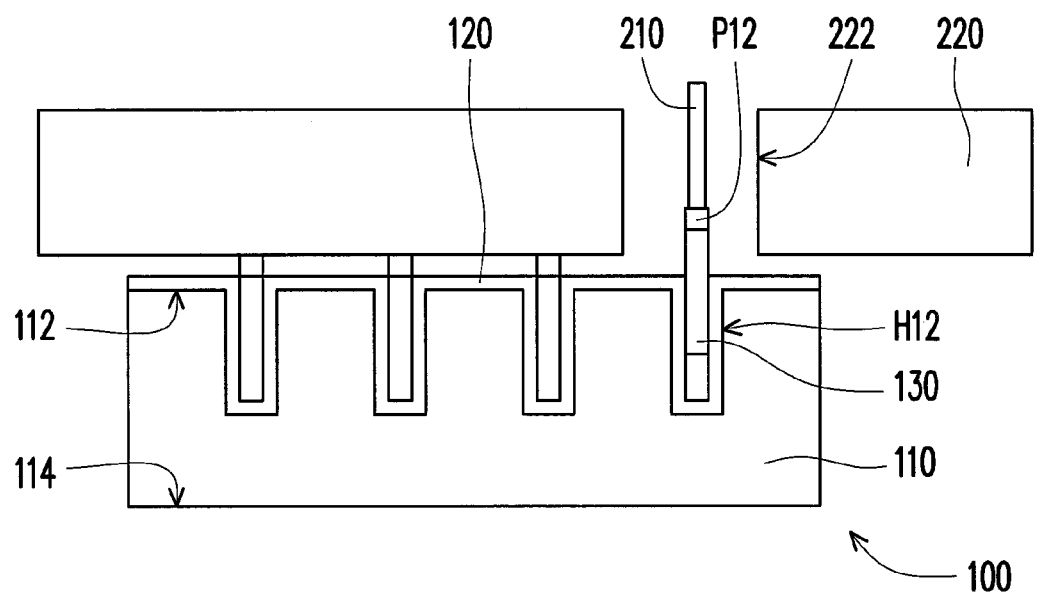

After the object to be tested 100 of FIG. 2D is provided, an external force is provided to the first surface of the conductive post 130, so as to perform a mechanical integrity test, thereby determining a mechanical integrity of the conductive post 130 according to whether the conductive post 130 is damaged, that is, testing a binding strength between the insulating layer 120, the conductive post 130, and the wall of the first blind hole H12 in which the conductive post 130 is located, as shown in FIG. 2H. Next, subsequent processes may be performed, for example, a first surface metal layer connected to the conductive post 130 is formed; the wafer 110 is bonded to a supporting substrate; the second surface of the wafer is polished, so as to expose a second surface of the conductive post; a second surface metal layer connected to the second surface of the conductive post 130 is formed; a plurality of bumps is formed on the second surface of the conductive post; the supporting substrate is removed; and the chips on the wafer 110 are connected to another element through the bumps etc. The subsequent processes are further described in the following with reference to FIGS. 2I to 2O.

The external force may be a pulling force manner, a pushing force manner, a suction force manner, or a bending manner. For example, the pulling force manner includes forming a photo-sensitive adhesive layer P10 on the first surface 112 of the wafer 110, as shown in FIG. 2E. The photo-sensitive adhesive layer P10 contacts with the first surface of the conductive post 130. Next, the photo-sensitive adhesive layer P10 is lithographically etched, so as to form an adhesive sheet P12 on the first surface of each conductive post 130, as shown in FIGS. 2F and 2G. Afterwards, a probe 210 is connected to one exposed end of the conductive post 130 through the adhesive sheet P12, and applies a pulling force to the conductive post 130. Here, a strength of the pulling force applied to the conductive post 130 by the probe 210 may be a preset value, if during the force application process, any one of the conductive post 130, the insulating layer 120, and the wall of the first blind hole H12 is damaged or any two of the three are peeled off from each other (as shown in FIG. 2H), it represents that the object to be tested 100 does not pass the mechanical integrity test. On the contrary, if the object to be tested 100 is not damaged by the pulling force applied to the conductive post 130 by the probe 210, it represents that the conductive post 130 is qualified in the mechanical integrity test. Here, the probe 210 is, for example, connected to the conductive post 130 through the adhesive sheet P12, but the disclosure is not limited hereto. In addition, before the probe 210 is connected to the conductive post 130 through the adhesive sheet P12, a gasket 220 may be firstly configured on the first surface 112. The gasket 220 has at least one opening 222, the opening 222 exposes the conductive post 130 in the first blind hole H12 to be tested, and the probe 210 contacts with the adhesive sheet P12 through the opening 222.

In the above steps, it is not limited that the first blind hole H12 to be tested is tested when being on the complete wafer 110, or after the part of the object to be tested 100 having the first blind hole H12 is cut, which fall within the protection scope of the disclosure.

After the mechanical integrity test as shown in FIG. 2H is performed, if the conductive post 130 is qualified in the mechanical integrity test, all the steps may be completed after the subsequent processes, the wafer of FIG. 3 is cut into chips 102, such that the conductive post 130 is electrically connected to an element 50, for example, for the wafer as shown in FIG. 2O. The conductive post 130 of the chip 102 is originally in the second blind hole H14 of FIG. 3, and before the stacked packaging is performed on the chip 102, two ends of the conductive post 130 may be exposed for being electrically connected. In the embodiment of FIG. 2O, one end of the conductive post 130 is electrically connected to another element 50 through the bumps, and the element 50 is also a chip. However, the conductive post 130 may also be electrically connected to the element 50 in other manners, and the element 50 may also be a line substrate or other elements.

Figure 2I:
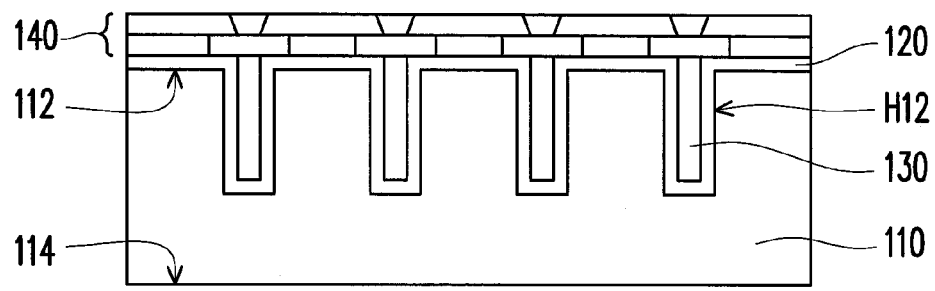
Figure 2J:
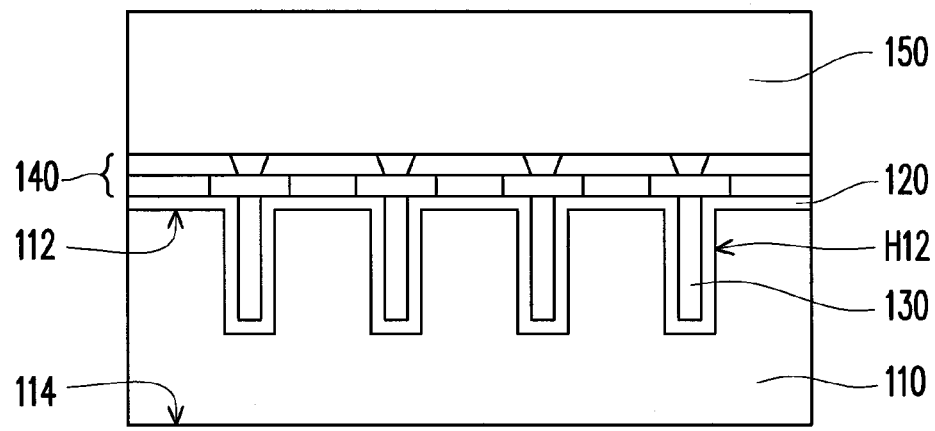
Figure 2K:
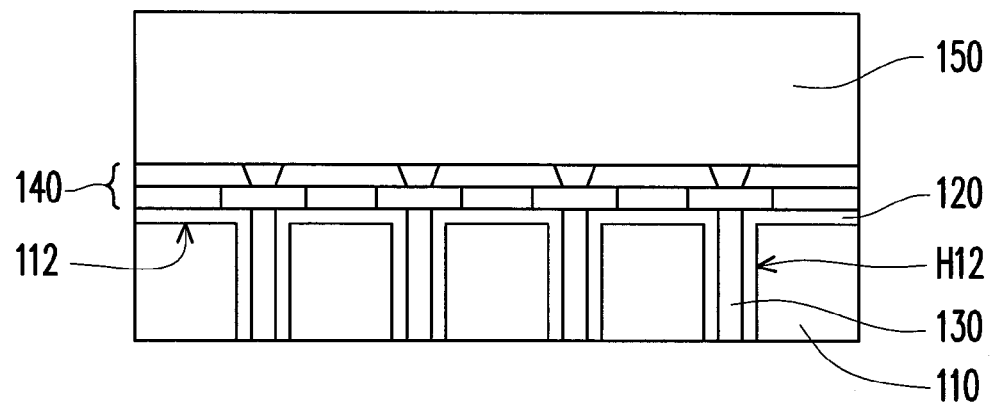
Figure 2L:
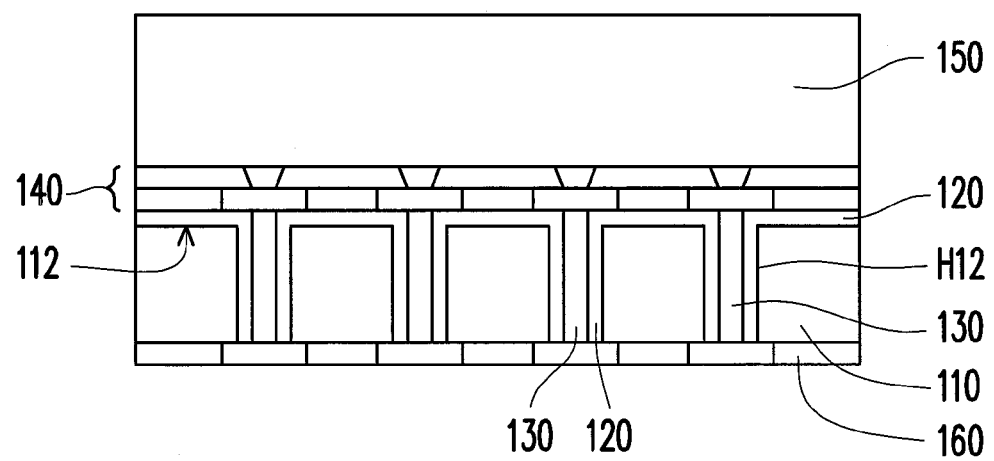
Figure 2M:
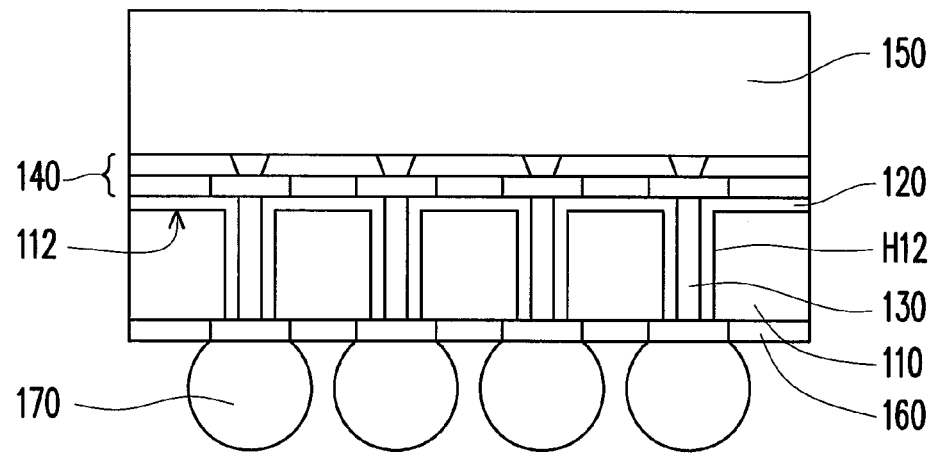
Figure 2N:
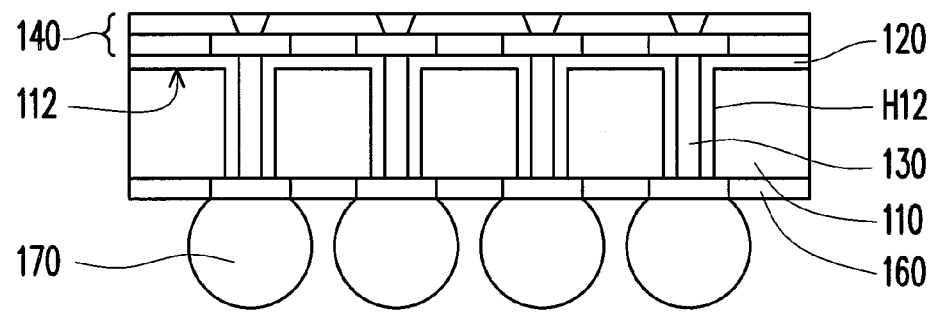
Figure 20:
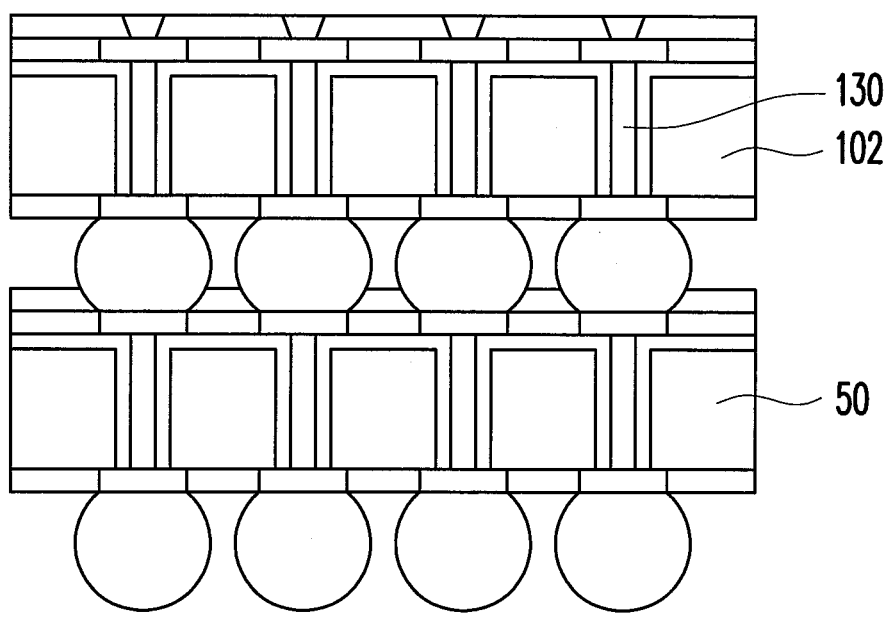

Next, steps of manufacturing the common semiconductor device capable of being performed during Steps 2H to 2O are exemplarily described, but the disclosure is not limited hereto. As shown in FIG. 2I, if the conductive post 130 is qualified in the mechanical integrity test, a circuit layer 140 may be formed on the insulating layer 120 and the conductive post 130. Afterwards, a supporting substrate 150 and the circuit layer 140 are bonded, as shown in FIG. 2J. The supporting substrate 150 is, for example, a silicon substrate or other substrates. Then, the supporting substrate 150 provides a supporting force, so as to thin the wafer 110 from the second surface 114, until the conductive post 130 is exposed, as shown in FIG. 2K. The step of thinning the wafer 110 is, for example, performed in a polishing manner. Next, a circuit layer 160 is formed on the second surface 114 of the thinned wafer 110, and the circuit layer 160 is electrically connected to at least a part of the conductive post 130, as shown in FIG. 2L. Then, bumps 170 are formed on the circuit layer 160, as shown in FIG. 2M. In not shown embodiments, the circuit layer 160 may include a sphere-bottom metal layer. Afterwards, the supporting substrate 150 is removed, as shown in FIG. 2N. After the step as shown in FIG. 2N is completed, the finished product may be used in the step of FIG. 2O.

In the above mentioned, the fabricating method of the semiconductor device according to an embodiment of the disclosure is completely introduced. Next, for the fabricating method of the semiconductor device according to other embodiments of the disclosure, steps used to replace the mechanical integrity test as shown in FIGS. 2E to 2H are introduced, and for the remaining steps, please refer to FIGS. 2A to 2D, and FIG. 2O.

Figure 4A:
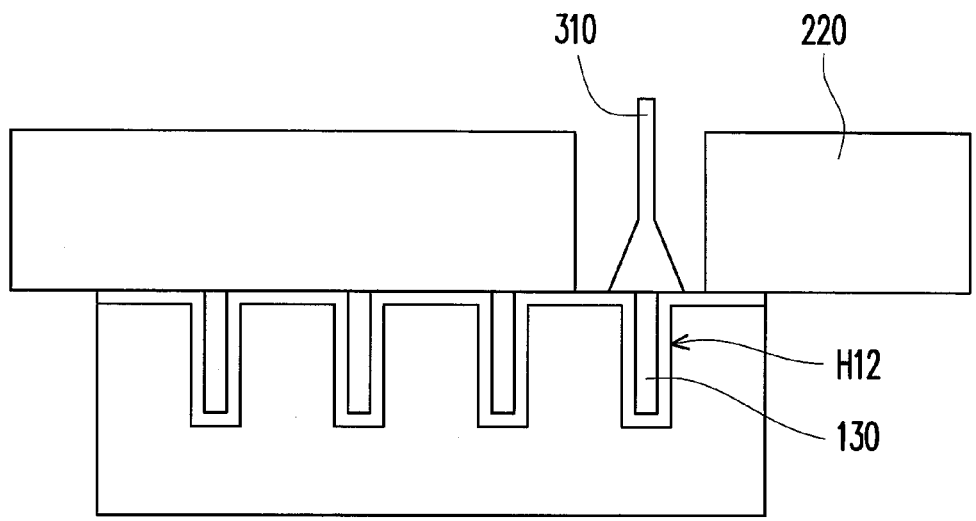
FIGS. 4A and 4B are schematic partial cross-sectional views of a mechanical integrity test of a fabricating method of a semiconductor device according to another embodiment of the disclosure.
Figure 4B:
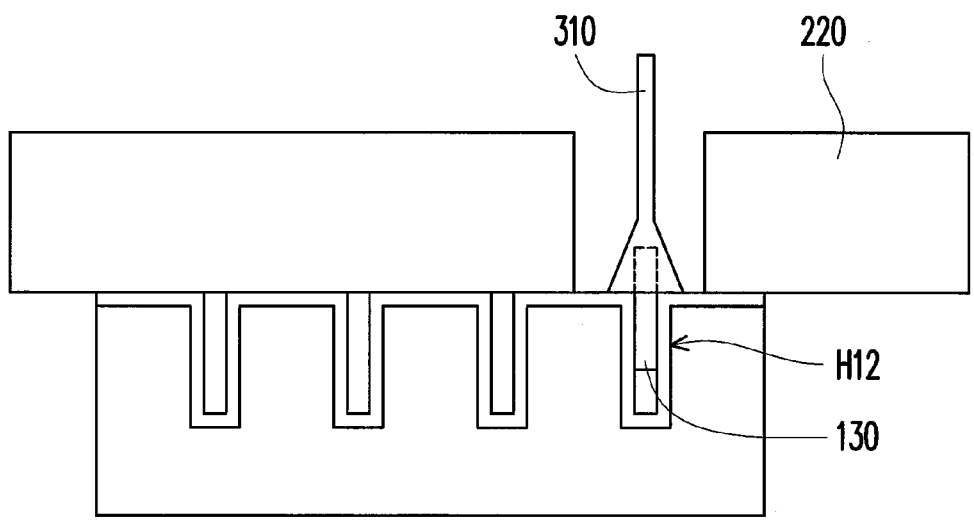

FIGS. 4A and 4B are schematic partial cross-sectional views of the mechanical integrity test of the fabricating method of the semiconductor device according to another embodiment of the disclosure. Referring to FIG. 4A, firstly, a suction nozzle 310 is aligned with the first surface of the conductive post 130 in the first blind hole H12. Next, as shown in FIG. 4B, the suction nozzle 310 applies a suction force having a preset strength to the first surface of the conductive post 130, so as to determine the mechanical integrity of the conductive post 130 according to whether the conductive post 130 is damaged, thereby determining whether the conductive post 130 is qualified in the mechanical integrity test.

Figure 5A:
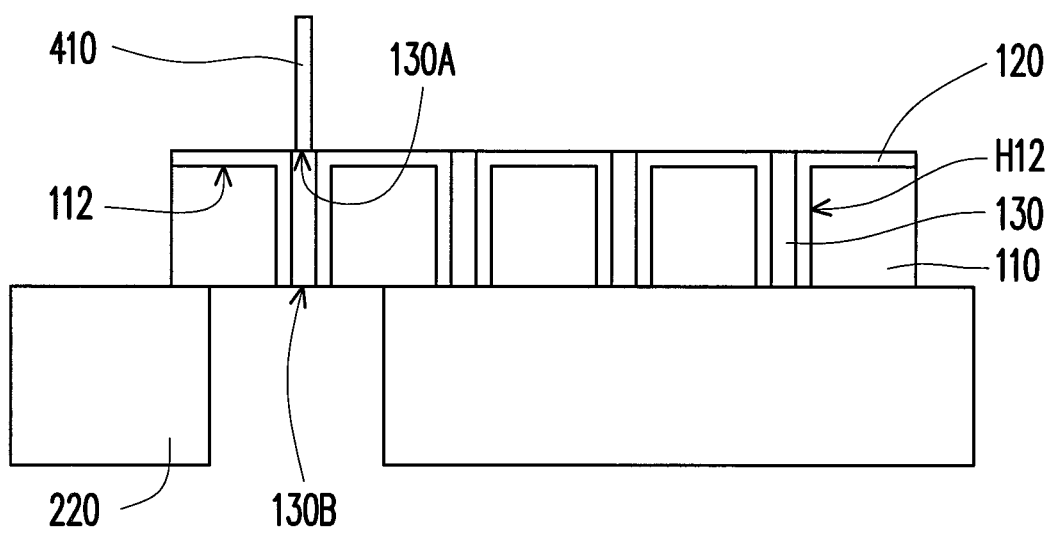
FIG. 5A is a schematic partial cross-sectional view of a mechanical integrity test of a fabricating method of a semiconductor device according to another embodiment of the disclosure.

FIG. 5A is a schematic partial cross-sectional view of the mechanical integrity test of the fabricating method of the semiconductor device according to another embodiment of the disclosure. After a part of the conductive layer 132 is removed through the CMP process or other processes (referring to FIG. 2C) and the conductive post 130 in the first blind hole H12 is kept (referring to FIG. 2D), the wafer 110 may be completely thinned until the conductive post 130 is exposed. Next, referring to FIG. 5A, a push-up needle 410 applies a pushing force to the first surface 130A of the conductive post 130, so as to determine the mechanical integrity of the conductive post 130 according to whether the conductive post 130 is damaged, thereby determining whether the conductive post 130 is qualified in the mechanical integrity test. In other embodiments, after the wafer 110 is completely thinned until the conductive post 130 is exposed, the push-up needle 410 applies the pushing force to the second surface 130B of the conductive post 130, that is, the push-up needle 410 applies the pushing force to the surface of the conductive post 130 being exposed after the wafer 110 is thinned, so as to determine the mechanical integrity of the conductive post 130.

Figure 5B:
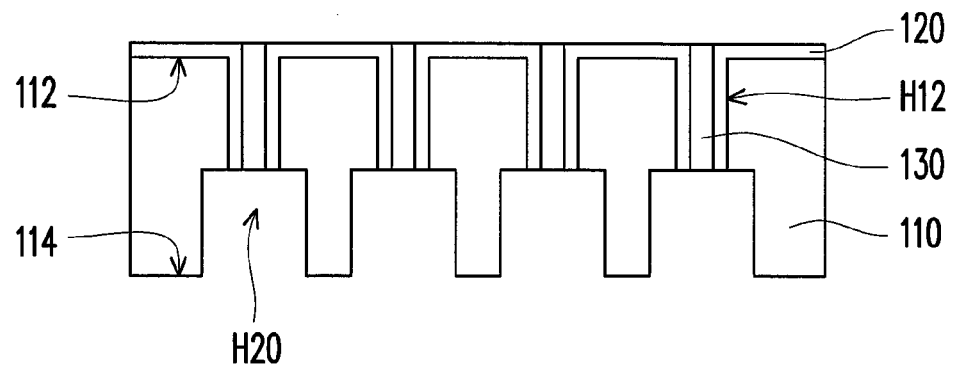
FIGS. 5B and 5C are schematic partial cross-sectional views of a mechanical integrity test of a fabricating method of a semiconductor device according to another embodiment of the disclosure.
Figure 5C:
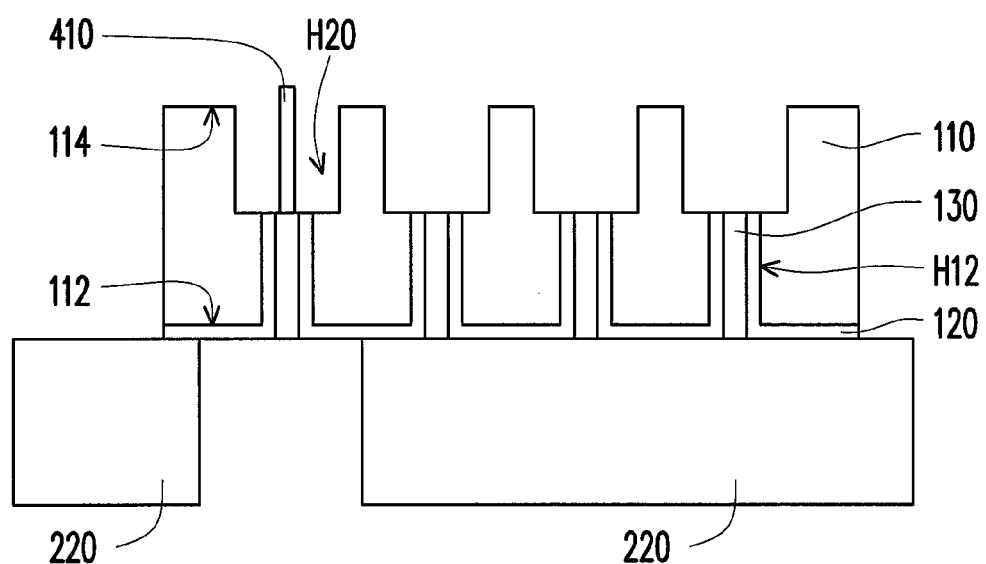

FIGS. 5B and 5C are schematic partial cross-sectional views of the mechanical integrity test of the fabricating method of the semiconductor device according to another embodiment of the disclosure. Referring to FIGS. 5B and 5C, this embodiment is different from the embodiment of FIG. 5A that the wafer 110 is not completely thinned, but a testing hole H20 is formed on the second surface 114 of the wafer 110. The testing hole H20 exposes the conductive post 130 in at least one first blind hole H12, as shown in FIG. 5B. Next, as shown in FIG. 5C, a push-up needle 410 applies a pushing force to the conductive post 130, so as to determine the mechanical integrity of the conductive post 130 according to whether the conductive post 130 is damaged, thereby determining whether the conductive post 130 is qualified in the mechanical integrity test. In this embodiment, the gasket 220 is also used, but the gasket 220 may also be not used.

Figure 6A:
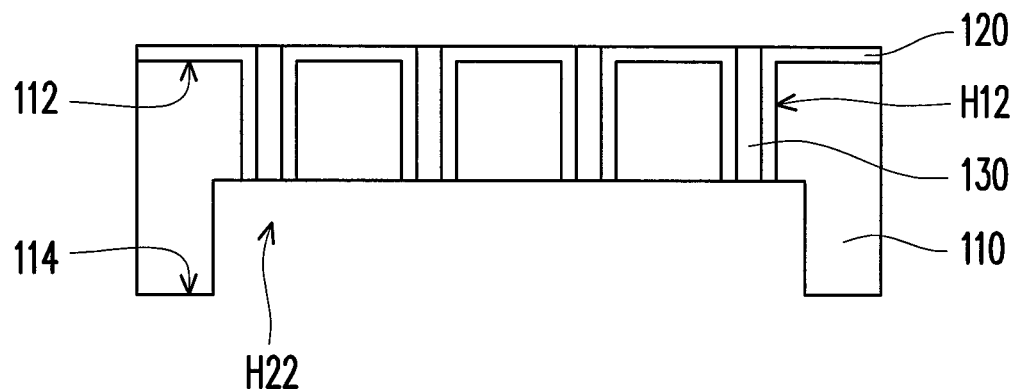
FIG. 6A is a schematic partial cross-sectional view of a mechanical integrity test of a fabricating method of a semiconductor device according to another embodiment of the disclosure.

FIG. 6A is a schematic partial cross-sectional view of the mechanical integrity test of the fabricating method of the semiconductor device according to another embodiment of the disclosure. Referring to FIG. 6A, firstly a testing hole H22 is formed on the second surface 114 of the wafer 110. The testing hole H22 exposes a plurality of conductive posts 130 in a plurality of first blind holes H12. Next, a push-up needle 412 applies a pushing force to the plurality of conductive posts 130, so as to determine the mechanical integrity of the conductive post 130 according to whether the conductive post 130 is damaged, thereby determining whether the plurality of conductive posts 130 is qualified in the mechanical integrity test. In this embodiment, a gasket 320 is also used, but the gasket 320 may also be not used. An opening 322 of the gasket 320 exposes the plurality of conductive posts 130.

Figure 6B:
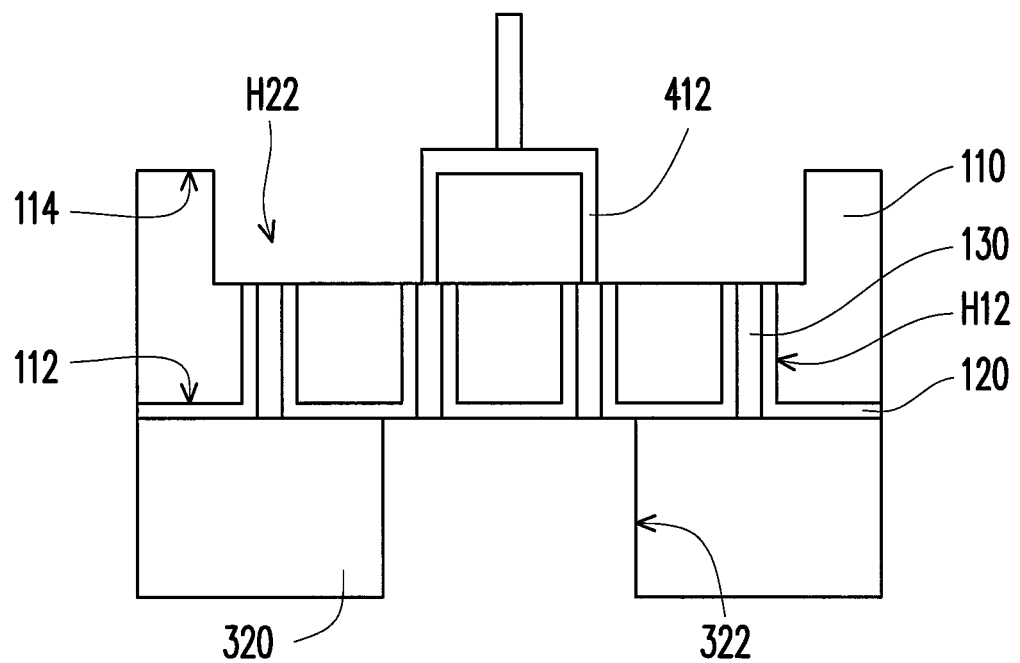
FIG. 6B is a schematic partial cross-sectional view of a mechanical integrity test of a fabricating method of a semiconductor device according to another embodiment of the disclosure.

FIG. 6B is a schematic partial cross-sectional view of the mechanical integrity test of the fabricating method of the semiconductor device according to another embodiment of the disclosure. Referring to FIG. 6B, this embodiment is different from the embodiment of FIG. 6A that the push-up needle 412 of this embodiment applies the pushing force to the conductive post 130 from the testing hole H22, and the first surface 112 of the wafer 110 contacts with the gasket 320. The gasket 320 is a fixture used to support the wafer 110.

Figure 7:
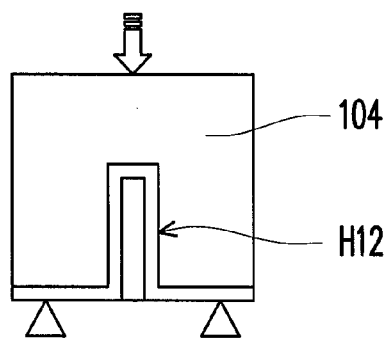
FIGS. 7 to 9 are schematic partial cross-sectional views of a mechanical integrity test of a fabricating method of a semiconductor device according to another three embodiments of the disclosure.
Figure 8:
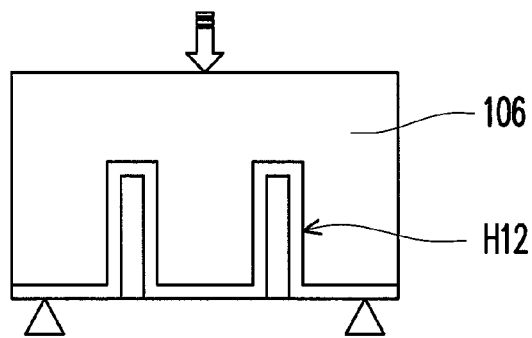
Figure 9:
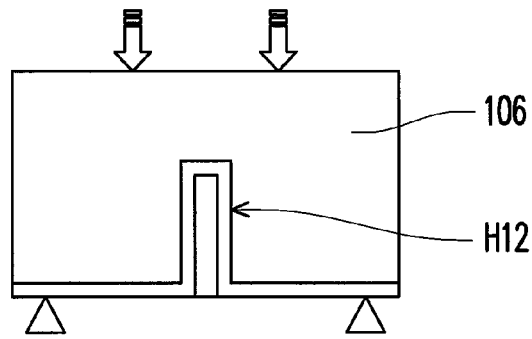

FIGS. 7 to 9 are schematic partial cross-sectional views of the mechanical integrity test of the fabricating method of the semiconductor device according to another three embodiments of the disclosure. Referring to FIG. 7, after the object to be tested 100 as shown in FIG. 2D is provided, a testing piece 104 may be separated from the object to be tested 100. The testing piece 104 includes a first blind hole H12. The mechanical integrity test of this embodiment is a three-point bending test performed on the testing piece 104. Referring to FIG. 8, after the object to be tested 100 as shown in FIG. 2D is provided, a testing piece 106 may be separated from the object to be tested 100. The testing piece 106 includes a plurality of first blind holes H12. The mechanical integrity test of this embodiment is a three-point bending test performed on the testing piece 106. Referring to FIG. 9, the mechanical integrity test of this embodiment is a four-point bending test performed on the testing piece 106.

In addition, before the mechanical integrity test of the embodiments of FIGS. 7 to 9 is performed, the CMP process or other processes may be performed, such that two ends of the conductive post 130 on the testing piece are exposed. Before the mechanical integrity test of the embodiments of FIGS. 5B and 6B is performed, the complete part to be tested may be separated from the object to be tested 100 of FIG. 2D, and the CMP process or other processes may be performed, such that two ends of the conductive post 130 on the testing piece are exposed.

Figure 10A:
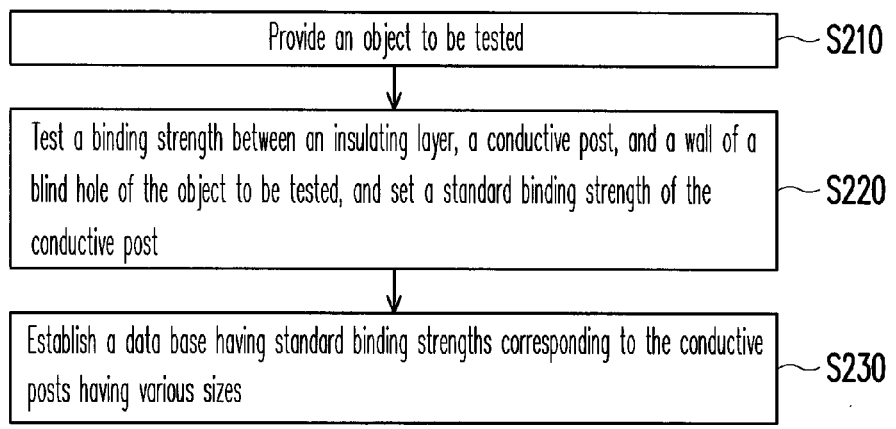
FIG. 10A is a flow chart of a testing method of a semiconductor device according to an embodiment of the disclosure.
Figure 10B:
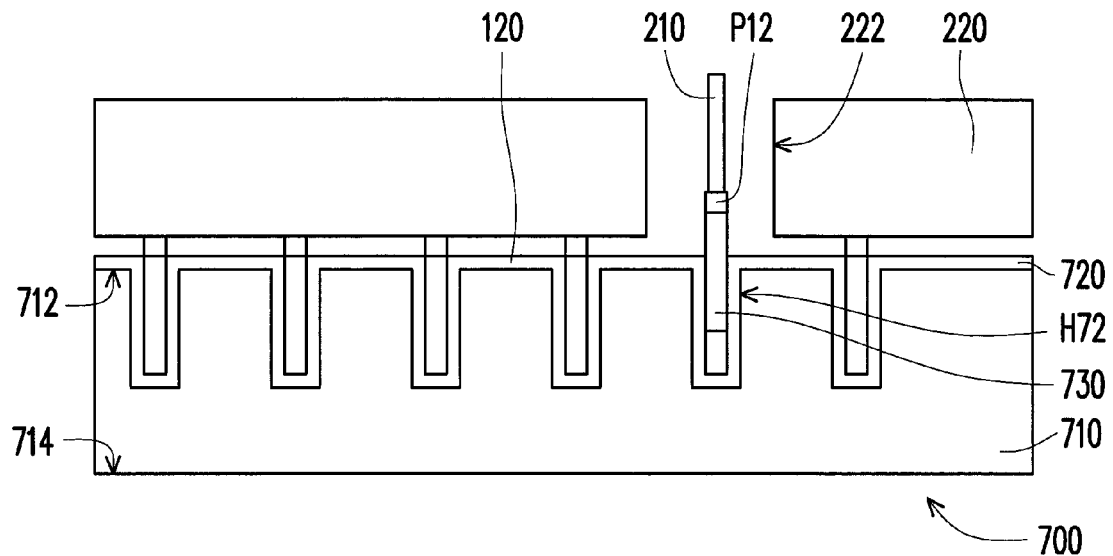
FIG. 10B is a schematic partial cross-sectional view of a mechanical integrity test in the testing method of FIG. 10A.

It is described in the above embodiments that in the mechanical integrity test, the strength of the force applied to the conductive post is a preset value. In the following, a testing method of a semiconductor device according to the disclosure is introduced, firstly, an object to be tested is provided, as shown in Step S110. Next, a binding strength between an insulating layer, a conductive post, and a wall of a blind hole in which the conductive post is located of the object to be tested is tested, as shown in Step S120. Then, conductive posts in chip regions of the object to be tested are electrically connected to an element, as shown in Step S130. In the disclosure, obtained data may be used to establish a data base of sizes and due binding strengths of the conductive posts. FIG. 10A is a flow chart of the testing method of the semiconductor device according to an embodiment of the disclosure, and FIG. 10B is a schematic partial cross-sectional view of a mechanical integrity test in the testing method of FIG. 10A. Referring to FIGS. 10A and 10B, the testing method of the semiconductor device according to this embodiment includes the following steps. An object to be tested 700 is provided, in Step S210. The object to be tested 700 includes a substrate 710, an insulating layer 720, and a plurality of conductive posts 730. The substrate 710 has a first surface 712 and a second surface 714 opposite to each other. The first surface 712 has a plurality of blind holes H72. The insulating layer 720 covers the first surface 712 and a wall of the blind hole H72. The conductive posts 730 fill inside the blind holes H72, and the insulating layer 720 is between the conductive post 730 and the wall of the blind hole H72. Like the object to be tested 100 of the embodiment of FIG. 3, the object to be tested 700 has a plurality of chip regions, but the object to be tested 700 may also be purely formed by the substrate 710, the insulating layer 720, and the conductive posts 730, but does not include the chip region, that is to say, the object to be tested 700 is purely used to test the integrity of the conductive post 730. In addition, in this embodiment, the plurality of conductive posts 730 is taken as an example, but in other embodiments, a single conductive post exists. In addition, the conductive posts 730 of this embodiment, for example, have the same size, but the conductive posts having various different sizes may also be provided on a single object to be tested, so as to perform the mechanical integrity test on the conductive posts having the various sizes for one time.

Next, the mechanical integrity test is performed, so as to test the binding strength between the insulating layer 720, the conductive post 730, and the wall of the blind hole H72, and set a standard binding strength of the conductive post 730, in Step S220. An actual performing manner of the mechanical integrity test performed here is similar to the embodiment of FIG. 2H, but the actual performing manners of other embodiments may also be adopted. In addition, the mechanical integrity test performed here is different from the above embodiments that the force applied to the conductive post 730 is gradually increased, until any one of the conductive post 730, the insulating layer 720, and the wall of the blind hole H72 is damaged or any two of the three are peeled off from each other, and the maximal applied force (damaging force) is recorded. Afterwards, the due standard binding strength of the conductive post 730 having the size is set according to the recorded maximal force. The standard binding strength is usually set according to the data after a plurality of maximal forces is obtained after the mechanical integrity test is performed on the conductive posts 73 having the same size for several times.

Afterwards, the above two steps are repeated, so as to set a plurality of standard binding strengths corresponding to the conductive posts 730 having various sizes, and establish a data base to store the plurality of standard binding strengths corresponding to the conductive posts 730 having various sizes, in Step S230.

After the data base is established, during the process of fabricating the semiconductor device, before the conductive post is electrically connected to a circuit layer or another element, the conductive post is tested by using the standard binding strength in the data base. That is to say, the data base is used when the mechanical integrity test is performed during the process of fabricating the semiconductor device of FIG. 1. Specifically, the mechanical integrity test is performed by using the standard binding strength corresponding to the size of the conductive post in the data base. Afterwards, the conductive post passing the mechanical integrity test and being not damaged is electrically connected to the element.

Figure 11:
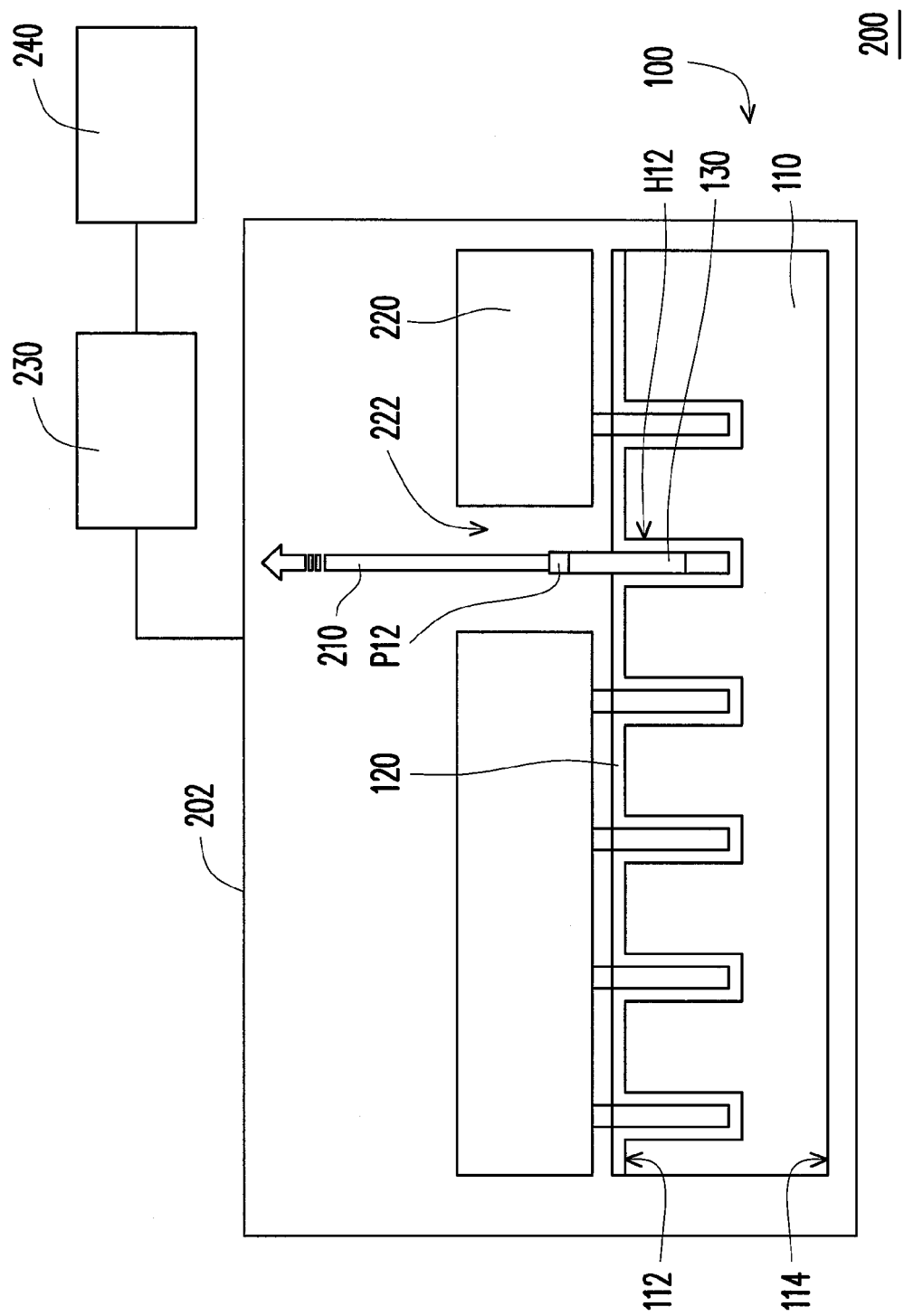
FIG. 11 is a schematic view of a mechanical integrity testing apparatus according to an embodiment of the disclosure.

FIG. 11 is a schematic view of a mechanical integrity testing apparatus according to an embodiment of the disclosure. Referring to FIG. 11, the mechanical integrity testing apparatus 200 according to this embodiment includes a testing fixture 202, a driver 230, and a data recorder 240. The testing fixture 202 is used to test a binding strength between an insulating layer 120, a conductive post 130, and a wall of a first blind hole H12 of an object to be tested 100, wherein the conductive post 130 is located in the first blind hole H12. The driver 230 is connected to and drives the testing fixture 202. The data recorder 240 is used to record a driving energy provided by the driver 230 to the testing fixture 202. The mechanical integrity testing apparatus 200 according to this embodiment is used to test the object to be tested 100 before a chip stacking process is performed, so as to determine that the conductive post 130 has a qualified integrity. In this manner, probabilities that a fabricated semiconductor device is defective due to the defective conductive posts are reduced, so as to lower a fabricating time and a fabricating cost. The mechanical integrity test of the disclosure may adopt a batch sampling test or may be performed during the process.

The testing fixture 202 includes a force application mechanism, and the force application mechanism applies an external force to the object to be tested, so as to determine a mechanical integrity of the conductive post according to whether the conductive post is damaged. The force application mechanism is a pulling force mechanism, a pushing force mechanism, a suction force mechanism, or a bending mechanism.

The testing fixture 202 of this embodiment is, for example, a pulling force mechanism including a probe 210, the probe 210 is connected to one exposed end of the conductive post 130 in the first blind hole H12, and pulls the conductive post 130 from the first blind hole H12. However, the conductive post 130 may also be in a through hole. The pulling force mechanism of this embodiment further includes a gasket 220 configured on the object to be tested 100. The gasket 220 has an opening 222, the opening 222 exposes the conductive post 130 in the first blind hole H12 to be tested, and the probe 210 contacts with the adhesive sheet P12 through the opening 222.

The driver 230 of this embodiment is a stretcher, so as to perform a stretching experiment through the probe 210. The data recorder 240 may record the driving energy provided by the driver 230 to the testing fixture 202 during the stretching experiment, in which the driving energy of this embodiment is a stretching force. The maximal stretching force recorded by the data recorder 240 is a damaging force resulting that any one of the conductive post 130, the insulating layer 120, and the wall of the first blind hole H12 is damaged or any two of the three are peeled off from each other. In addition, the probe 210 may apply the stretching force of a preset strength to the conductive post 130, so as to determine whether the conductive post 130 may bear the stretching force of the preset strength, and the real damaging force required by the damage is not necessarily measured.

Figure 12:
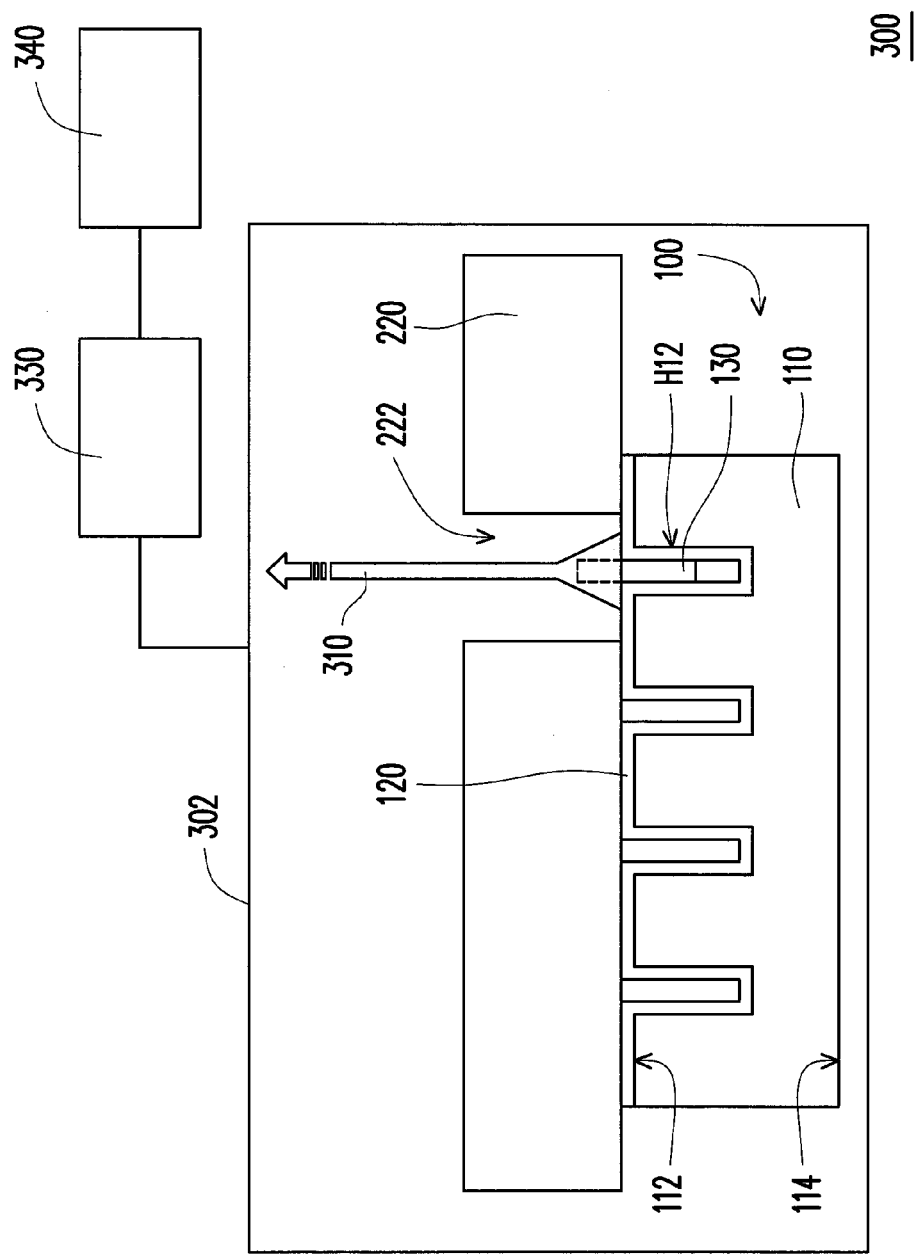
FIG. 12 is a schematic view of a mechanical integrity testing apparatus according to another embodiment of the disclosure.

FIG. 12 is a schematic view of a mechanical integrity testing apparatus according to another embodiment of the disclosure. Referring to FIG. 12, the mechanical integrity testing apparatus 300 according to this embodiment is similar to the mechanical integrity testing apparatus 200 of FIG. 11, such that differences are introduced in the following. A testing fixture 302 of this embodiment is, for example, a suction force mechanism including a suction nozzle 310, the suction nozzle 310 is aligned with the conductive post 130 in the first blind hole H12, and pulls the conductive post 130 from the first blind hole H12. A driver 330 of this embodiment is a vacuum pumping device, for providing a suction force required by the suction nozzle 310. A data recorder 340 may record a suction force provided by the driver 330 to the testing fixture 302 during the mechanical integrity test. The maximal suction force recorded by the data recorder 340 is a damaging force resulting that any one of the conductive post 130, the insulating layer 120, and the wall of the first blind hole H12 is damaged or any two of the three are peeled off from each other. In addition, the suction nozzle 310 may apply the suction force of a preset strength to the conductive post 130, so as to determine whether the conductive post 130 may bear the suction force of the preset strength, and the real damaging force required by the damage is not necessarily measured.

Figure 13A:
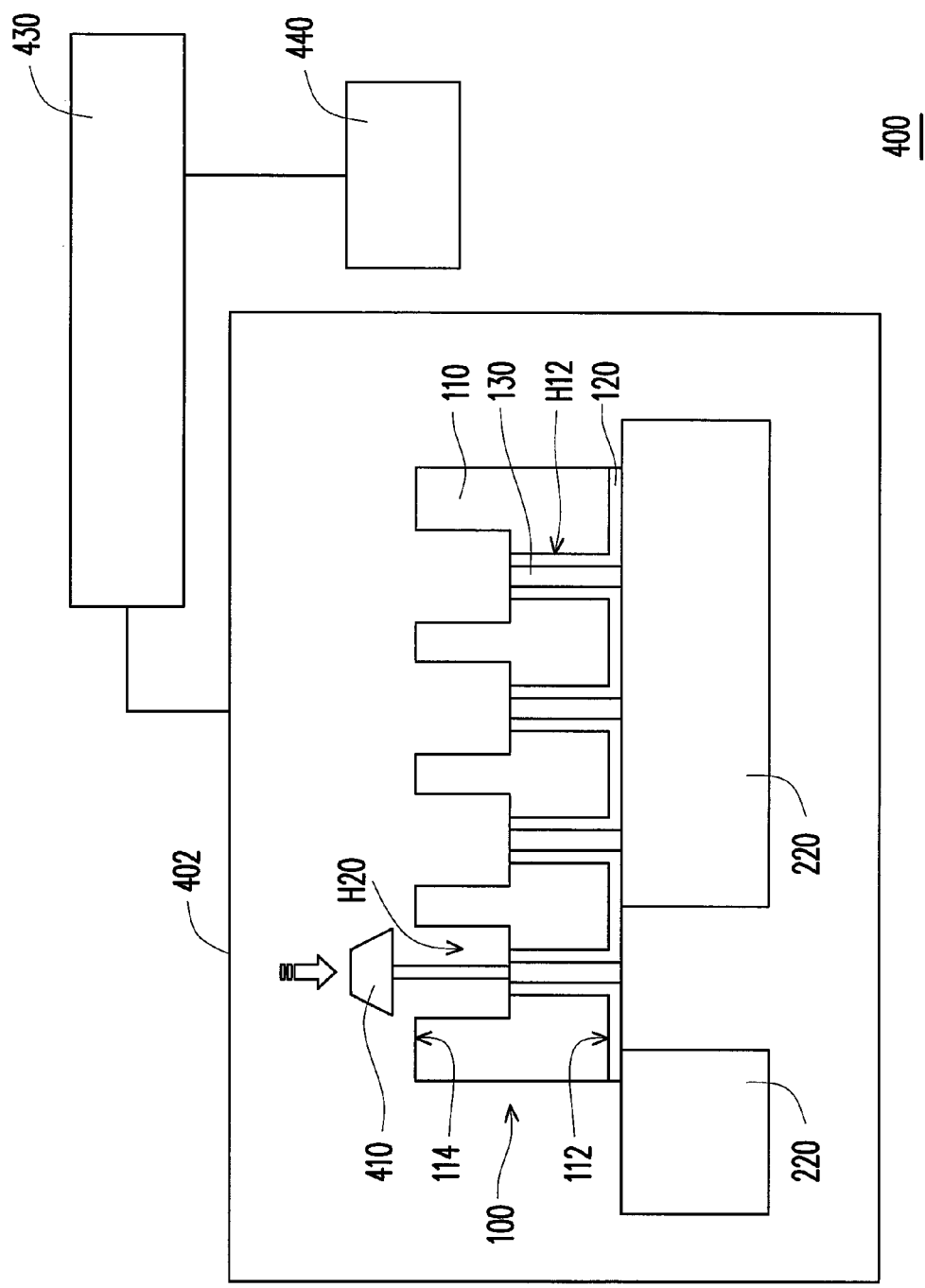
FIG. 13A is a schematic view of a mechanical integrity testing apparatus according to another embodiment of the disclosure.

FIG. 13A is a schematic view of a mechanical integrity testing apparatus according to another embodiment of the disclosure. Referring to FIG. 13A, the mechanical integrity testing apparatus 400 according to this embodiment is similar to the mechanical integrity testing apparatus 200 of FIG. 11, such that differences are introduced in the following. A testing fixture 402 of this embodiment is, for example, a pushing force mechanism including a push-up needle 410, for ejecting the conductive post 130 from the first blind hole H12. A driver 430 of this embodiment is an ejector, for performing a pushing experiment through the push-up needle 410. A data recorder 440 may record a pushing force provided by the driver 430 to the testing fixture 402 during the mechanical integrity test. The maximal pushing force recorded by the data recorder 440 is a damaging force resulting that any one of the conductive post 130, the insulating layer 120, and the wall of the first blind hole H12 is damaged or any two of the three are peeled off from each other. In addition, the push-up needle 410 may apply the pushing force of a preset strength to the conductive post 130, so as to determine whether the conductive post 130 may bear the suction force of the preset strength, and the real damaging force required by the damage is not necessarily measured. In this embodiment, the object to be tested 100 is configured between the gasket 220 and the push-up needle 410.

Figure 13B:
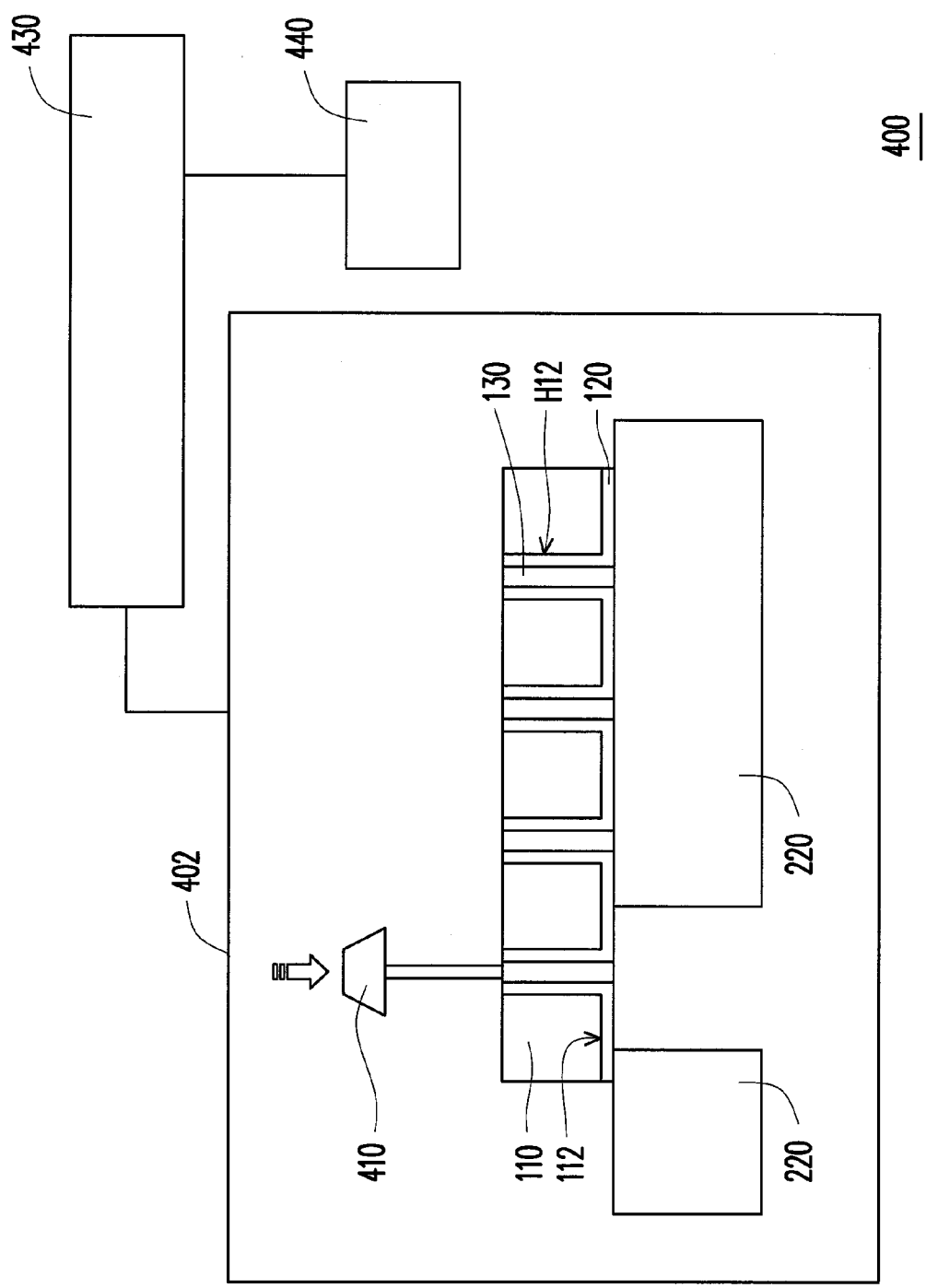
FIG. 13B is a schematic view of another mechanical integrity test performed by the mechanical integrity testing apparatus of FIG. 13A.

FIG. 13B is a schematic view of another mechanical integrity test performed by the mechanical integrity testing apparatus of FIG. 13A. Referring to FIG. 13B, this embodiment is different from the embodiment of FIG. 13A that in this embodiment, after the wafer 110 is completely thinned until the conductive post 130 is exposed, the push-up needle 410 applies the pushing force to the conductive post 130, so as to determine whether the conductive post 130 is qualified in the mechanical integrity test.

Figure 14:
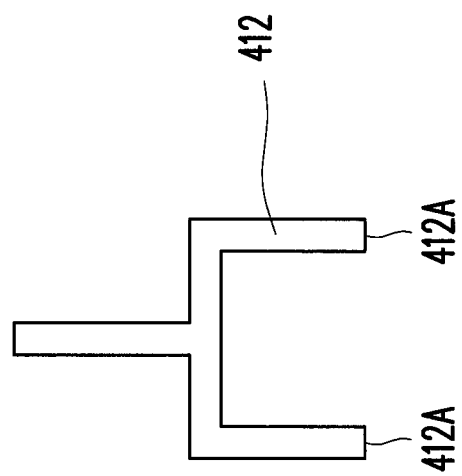
FIG. 14 shows a push-up needle of a mechanical integrity testing apparatus according to another embodiment of the disclosure.

In another embodiment, the push-up needle 412 has a plurality of ejection ends 412A, for ejecting the plurality of conductive posts from the plurality of holes in which the conductive posts are located, as shown in FIG. 14.

Figure 15:
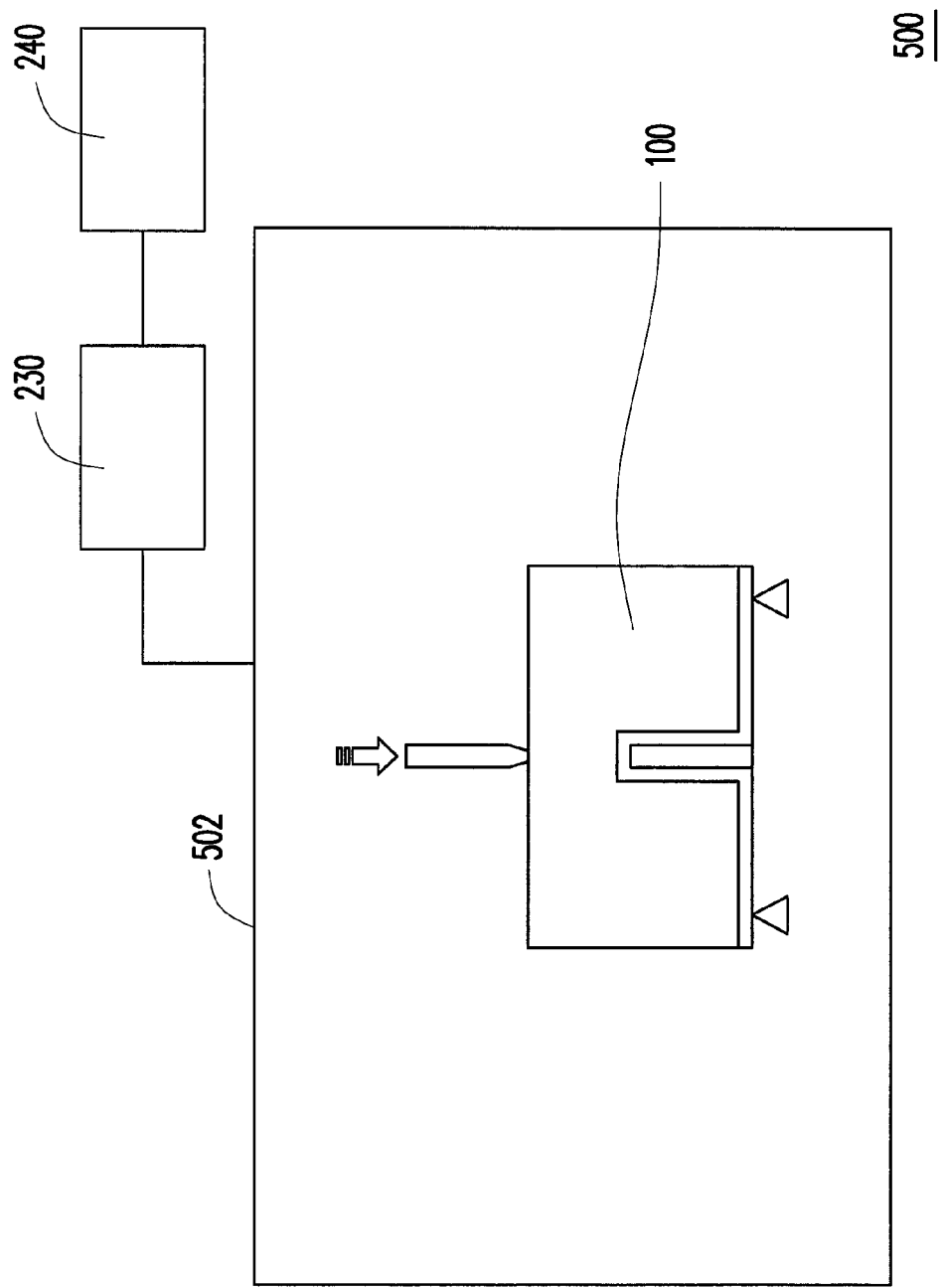
FIG. 15 is a schematic view of a mechanical integrity testing apparatus according to another embodiment of the disclosure.
Figure 16:
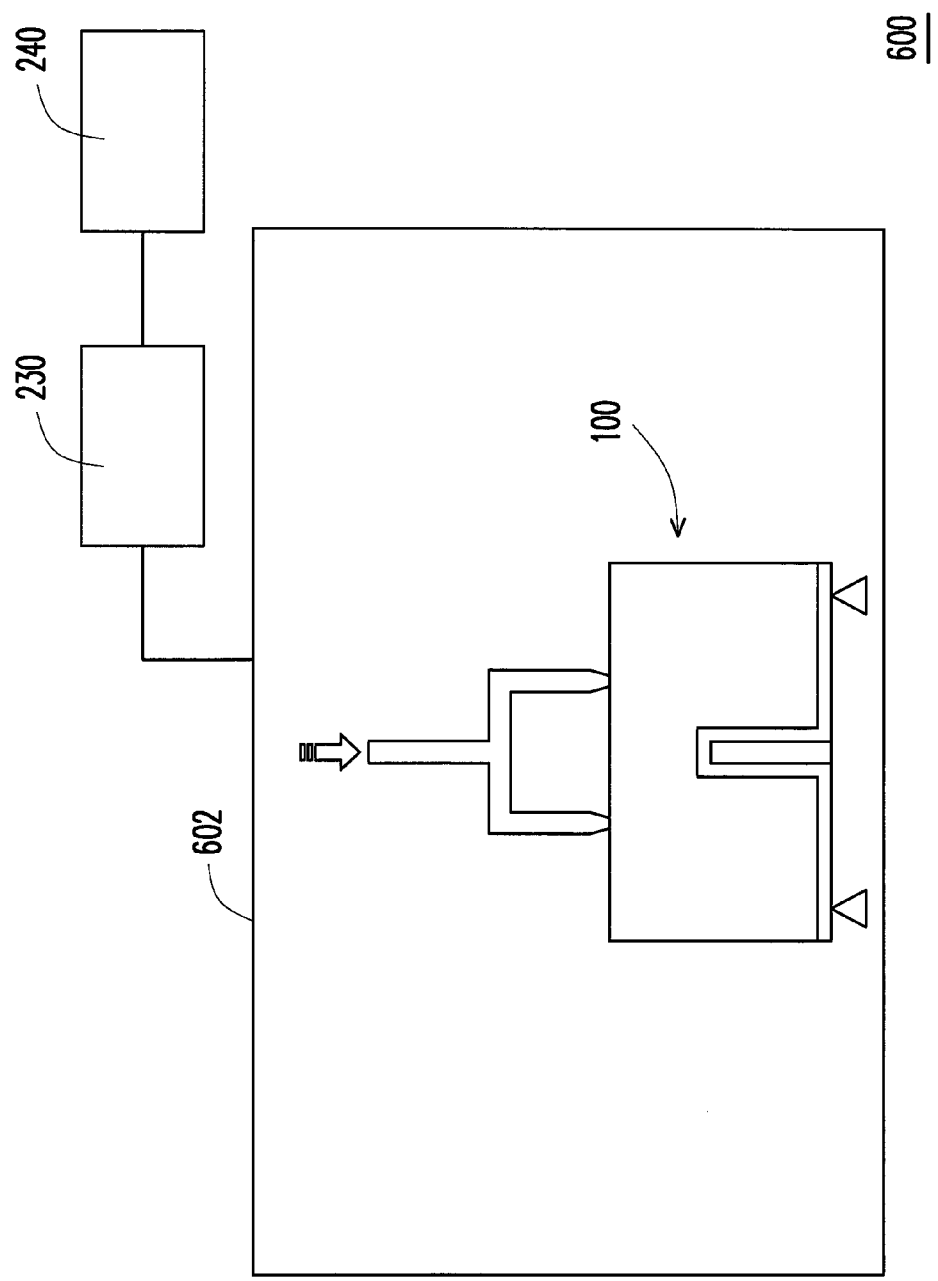
FIG. 16 is a schematic view of a mechanical integrity testing apparatus according to another embodiment of the disclosure.
Figure 17:
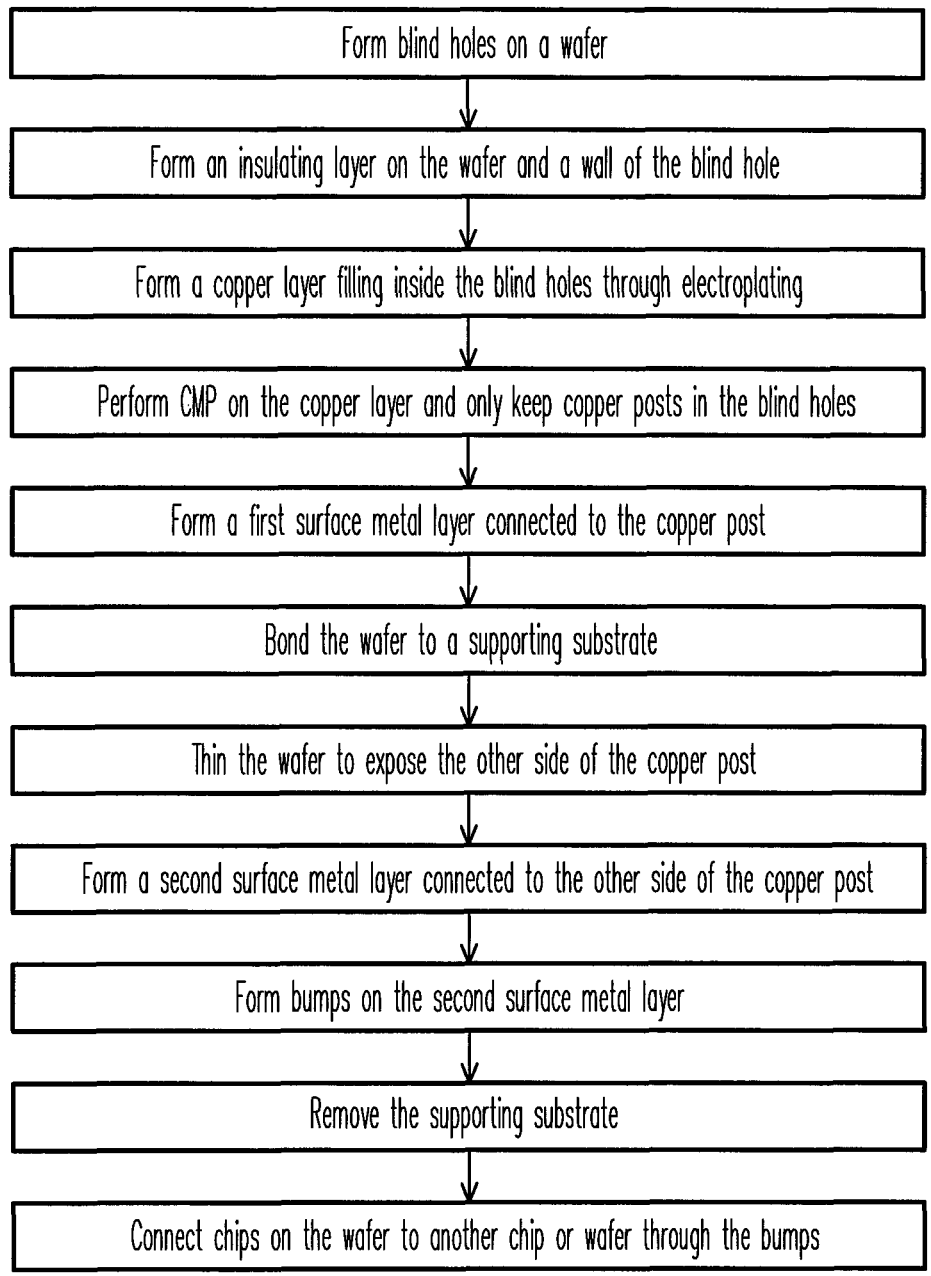
FIG. 17 is a schematic view of a conventional 3DIC integration process.

FIG. 15 is a schematic view of a mechanical integrity testing apparatus according to another embodiment of the disclosure. Referring to FIG. 15, the mechanical integrity testing apparatus 500 according to this embodiment is similar to the mechanical integrity testing apparatus 200 of FIG. 11, and differences are introduced in the following. A testing fixture 502 of this embodiment is, for example, a bending mechanism being a three-point bending mechanism, for performing a three-point bending test on the object to be tested 100. In another embodiment, a testing fixture 602 of a mechanical integrity testing apparatus 600 is, for example, a bending mechanism being a four-point bending mechanism, as shown in FIG. 16.

To sum up, in the fabricating method of the semiconductor device according to the disclosure, firstly, the binding strength between the insulating layer, the conductive post, and the wall of the blind hole is tested, and after it is confirmed that the binding strength is qualified, the chips are electrically connected to another element through the conductive posts, thereby avoiding increasing the processing cost due to the defective conductive posts.

The disclosure is used to avoid a situation that a TSV structure is found to be invalid when a chip including TSVs is 3D stacked subsequently.

The disclosure is directed to a fabricating method of a semiconductor device, capable of solving a problem that a defective TSV results in that a fabricating cost of the semiconductor device is increased.

It will be apparent to those skilled in the art that various modifications and variations can be made to the structure of the disclosed embodiments without departing from the scope or spirit of the invention. In view of the foregoing, it is intended that the invention cover modifications and variations of this invention provided they fall within the scope of the following claims and their equivalents.

What is claimed is:

1. A fabricating method of a semiconductor device, comprising:
   providing a wafer comprising a first surface and a second surface;
   forming a plurality of blind holes on the first surface of the wafer;
   forming an insulating layer on walls of the blind holes and the first surface of the wafer;
   forming a conductive post in at least one of the blind holes, and enabling a first surface of the conductive post to be exposed out of the insulating layer; and
   providing an external force to the first surface of the conductive post, and determining a mechanical integrity of the conductive post according to whether the conductive post is damaged.

2. The fabricating method of a semiconductor device according to claim 1, wherein the external force is a pulling force manner, a pushing force manner, a suction force manner, or a bending manner.

3. The fabricating method of a semiconductor device according to claim 2, wherein the pulling force manner comprises:
   connecting a probe to the first surface of the conductive post; and
   applying a pulling force to the conductive post by the probe.

4. The fabricating method of a semiconductor device according to claim 3, wherein the step of connecting the probe to the conductive post comprises:
   forming a photo-sensitive adhesive layer on the first surface of the wafer;
   lithographically etching the photo-sensitive adhesive layer, so as to form an adhesive sheet on the first surface of each conductive post; and
   connecting the probe to the first surface of the conductive post through the adhesive sheet.

5. The fabricating method of a semiconductor device according to claim 4, wherein before the step of connecting the probe to the first surface of the conductive post through the adhesive sheet, the method further comprises configuring a gasket on the first surface, wherein the wafer comprises a plurality of chip regions, the blind holes comprises a plurality of first blind holes and a plurality of second blind holes, the first blind holes are outside the chip regions, the second blind holes are inside the chip regions, the gasket comprises at least one opening, the opening exposes the conductive post in one of the first blind holes, such that the probe contacts with the adhesive sheet through the opening.

6. The fabricating method of a semiconductor device according to claim 2, wherein the suction force manner comprises:
   aligning a suction nozzle with the first surface of the conductive post in one of the blind holes; and
   applying a suction force to the first surface of the conductive post by the suction nozzle.

7. The fabricating method of a semiconductor device according to claim 2, wherein the pushing force manner comprises:
   enabling the wafer to expose the conductive post in one of the blind holes; and
   applying a pushing force to the first surface or a second surface of the conductive post by a push-up needle.

8. The fabricating method of a semiconductor device according to claim 7, wherein the manner of enabling the wafer to expose the conductive post in one of the blind holes comprises forming a testing hole on the second surface of the wafer, wherein the testing hole exposes the conductive post in one of the blind holes.

9. The fabricating method of a semiconductor device according to claim 1, wherein the conductive post is disposed in one of the blind holes of the wafer, so as to form an object to be tested.

10. The fabricating method of a semiconductor device according to claim 9, wherein before the step of providing the external force to the first surface of the conductive post, and determining the mechanical integrity of the conductive post according to whether the conductive post is damaged, the method further comprises separating a testing piece from the object to be tested, wherein the testing piece comprises at least one of the blind holes formed with the conductive post therein, and a mechanical integrity test comprises a three-point bending test or a four-point bending test performed on the testing piece.

11. The fabricating method of a semiconductor device according to claim 10, before the step of providing the external force to the first surface of the conductive post, and determining the mechanical integrity of the conductive post according to whether the conductive post is damaged, the method further comprises enabling two ends of at least one conductive post on the testing piece to be exposed.

* * * * *